United States Patent
Stucchi et al.

(10) Patent No.: US 11,566,085 B2
(45) Date of Patent: Jan. 31, 2023

(54) PROCESS FOR THE PURIFICATION OF HYALURONIC ACID SALT, CONDUCTED IN ORGANIC SOLVENT

(71) Applicant: BMG PHARMA S.P.A., Milan (IT)

(72) Inventors: Luca Stucchi, Torviscosa (IT); Fabrizio Picotti, Torviscosa (IT); Alessandra Sechi, Torviscosa (IT); Rita Gianni, Monrupino (IT)

(73) Assignee: BMG PHARMA S.P.A., Milan (IT)

( * ) Notice: Subject to any disclaimer, the term of this patent is extended or adjusted under 35 U.S.C. 154(b) by 0 days.

(21) Appl. No.: 17/755,120

(22) PCT Filed: Oct. 19, 2020

(86) PCT No.: PCT/EP2020/079319
§ 371 (c)(1),
(2) Date: Apr. 21, 2022

(87) PCT Pub. No.: WO2021/078669
PCT Pub. Date: Apr. 29, 2021

(65) Prior Publication Data
US 2022/0348692 A1    Nov. 3, 2022

(30) Foreign Application Priority Data
Oct. 24, 2019   (IT) .................. 102019000019724

(51) Int. Cl.
*C08B 37/08* (2006.01)
*A61K 31/728* (2006.01)

(52) U.S. Cl.
CPC ........ *C08B 37/0072* (2013.01); *A61K 31/728* (2013.01)

(58) Field of Classification Search
CPC .................. C08B 37/0072; A61K 31/728
See application file for complete search history.

(56) References Cited

U.S. PATENT DOCUMENTS 6,031,017 A * 2/2000 Waki ............... A61L 31/042
522/89
6,946,551 B2 * 9/2005 Long ............... A61K 8/982
536/55.1

FOREIGN PATENT DOCUMENTS

| EP | 2039777 A1 | 3/2009 |
| JP | 2006-321890 | * 11/2006 |
| WO | 2009080220 A1 | 7/2009 |

OTHER PUBLICATIONS

Machine translation of JP 2006-321890. (Year: 2006).*
Search Report and Written Opinion of PCT/EP2020/079319 dated Jan. 28, 2021.

* cited by examiner

*Primary Examiner* — Leigh C Maier
(74) *Attorney, Agent, or Firm* — Silvia Salvadori, P.C.; Silvia Salvadori

(57) ABSTRACT

The present invention relates to a process for the preparation of pharmaceutical, injectable or ophthalmic grade hyaluronic acid, or a salt thereof, for use in the dermocosmetic or pharmaceutical field or in medical devices, which comprises dissolution of hyaluronic acid or a salt thereof in organic solvent, a heat cycle, and recovery of the product by precipitation and successive washes in organic solvents.

9 Claims, No Drawings

PROCESS FOR THE PURIFICATION OF HYALURONIC ACID SALT, CONDUCTED IN ORGANIC SOLVENT

This application is a U.S. national stage of PCT/EP2020/079319 filed on 19 Oct. 2020, which claims priority to and the benefit of Italian Patent Application No. 102019000019724 filed on 24 Oct. 2019, the contents of which are incorporated herein by reference in their entireties.

The present invention relates to a process for the preparation of pharmaceutical, injectable or ophthalmic grade hyaluronic acid, or a salt thereof, for use in the dermocosmetic or pharmaceutical field or in medical devices, which comprises dissolution of hyaluronic acid or a salt thereof in organic solvent, a heat cycle, and recovery of the product by precipitation and successive washes in organic solvents.

The present invention discloses the process for purification of hyaluronic acid (HA) or a salt thereof by heat treatment in an organic medium which surprisingly removes both bacteria and endotoxins, namely the lipopolysaccharides present in the outer membrane of the gram-negative bacteria responsible for the in vivo inflammatory response, and protects the native hyaluronic acid against hydrolysis-induced degradation of the polysaccharide chain. The hyaluronic acid prepared by said process has a microbiological profile compatible with pharmaceutical, injectable or ophthalmic grade hyaluronic acids. The process offers advantages in chemical and biological terms, by preventing hydrolytic degradation because it is conducted in a non-aqueous organic solvent. The process also has a low environmental and economic impact because it does not require the high volumes typical of existing procedures, and allows complete recovery of the solvents for reuse. Finally, the extreme simplicity of the process, which does not involve expensive filtration, diafiltration or ion-exchange techniques, has a highly favorable effect on its cost, thus expanding the possible economically sustainable applications of a sodium hyaluronate with a high degree of purity, and therefore increasing the safety of products containing said polysaccharide, which are generally intended for human use.

STATE OF THE ART

Hyaluronic acid is a glycosaminoglycan consisting of repeating units of glucuronic acid and N-acetylglucosamine bonded together, alternatively, via glycoside bonds $\beta1\rightarrow4$ and $\beta1\rightarrow3$. It is an essential element of connective tissue, and is also present in synovial fluid, vitreous humour and umbilical cord.

Hyaluronic acid was isolated by Karl Meyer and John Palmer in 1934, and has numerous topical uses, injectable uses in implants (subcutaneous or intra-articular), and uses in the ophthalmic field. The acceptable bioburden depends on the final application of the hyaluronic acid: for topical applications or applications to the external mucosa, the "cosmetic grade" is used with a limit, defined as the Total Aerobic Microbic Count (TAMC) and Total Yeast and Mold Count (TYMC), on the number of bacterial colonies and yeasts and molds (up to $10^3$ colony-forming units per gram, or CFU/g), while the endotoxin unit limit has not been defined; for more invasive applications, the "pharmaceutical", "ophthalmic" or "injectable" grade is used, with stricter bioburden limits on the bacteria count and an endotoxin content of less than 0.5 EU/mg for parenteral applications and 0.05 EU/mg for intra-articular or intraocular applications. In view of the numerous applications of hyaluronic acid in the ophthalmic field and as a subdermal or articular injectable, the importance of research into simple, reliable, cheap methods of purifying hyaluronic acid is obvious.

WO2013/132506 discloses a method of purification from endotoxins by treatment with bentonite and filtration through activated carbon; WO00/44925 reports a tangential filtration method followed by sterilising filtration, while US2018/014041 uses diafiltration techniques on highly dilute solutions; and CA02225866 discloses negatively-charged resins used in sequence. All said processes are highly complex and use very expensive instrumentation and equipment (ultrafiltration units, ion-exchange columns and freeze-dryers) which makes them difficult to apply in anything other than extremely expensive industrial processes. In the case of dilute solutions (US2018/014041), the necessary volumes also have a high environmental impact.

EP 2865395 discloses a heat cycle in water followed by sterilising filtration. The process times described, ranging from 1 to 6 days, limit the potential of the process in view of the sensitivity of hyaluronic acid to temperature-dependent hydrolytic degradation.

EP2039777 uses the extraction process in organic solvent. It consists of a heterogeneous-phase process involving a high risk of inefficacy in view of the difficulty of completely eliminating microbiological impurities trapped in the amorphous solid, which consists of hyaluronic acid, albeit swollen.

Finally, U.S. Pat. No. 5,079,236 discloses the preparation of an injectable formulation, starting with a hyaluronic acid that is already microbiologically pure, by dissolving it in water to a suitable concentration in the presence of paraben preservatives. The process described in that case does not involve actual purification, but is a preservation process using ingredients which may have contraindications in terms of safety, especially in the case of injectable medical devices.

In general, all the known processes involve the use of machines which are difficult to introduce into industrial processes, due to both their technological complexity and their high cost. Moreover, said processes use large volumes of aqueous and organic solvent, with repercussions on the disposal and recovery costs and environmental impact.

Moreover, as all said processes are conducted in water or in aqueous and organic mixtures, and require long process times and temperatures exceeding room temperature, they have adverse effects on the molecular weight of the hyaluronic acid due to hydrolytic degradation.

Finally, a process has never been described which involves using a cosmetic grade hyaluronic acid or a salt thereof and increasing its microbiological purity to a level compatible with pharmaceutical, injectable or ophthalmic grade hyaluronic acids.

A process has now been found which produces hyaluronic acid or a salt thereof starting with a product with a lower (cosmetic) grade of microbiological purity, giving rise to a product with a microbiological profile compatible with pharmaceutical, injectable or ophthalmic grade hyaluronic acids.

As the process according to the present invention is conducted in homogeneous phase in organic solvent, it eliminates the complexity of the existing processes. The efficiency of the process limits the solvent volumes used, with favourable economic and environmental effects. The use of non-aqueous systems prevents the typical hydrolytic degradation that adversely affects the standard processes. The possibility of starting with a hyaluronic acid or salt thereof having a lower (cosmetic) grade of microbiological purity to obtain a higher grade of microbiological purity exponentially increases the versatility of the process, because it is not associated with a fermentation process, increases the value of the starting substrate by means of a cost-effective process with a low environmental impact, and potentially enables different levels of microbiological purity to be obtained from the same starting material, thus allowing its use in application fields of different levels of invasiveness, with obvious repercussions in terms of efficiency, safety and cost.

DESCRIPTION OF THE INVENTION

The object of the present invention is a process for the preparation of a pharmaceutical, injectable or ophthalmic grade hyaluronic acid, or a salt thereof, comprising the following steps:
- a) dissolving hyaluronic acid or a salt thereof at a temperature ranging between 50° C. and 100° C. in a solvent selected from dimethylformamide, dimethylacetamide, N-methylpyrrolidone and formamide, and maintaining the solution under stirring at said temperature for a period ranging from 1 hour to 48 hours;
- b) reducing the temperature to room temperature and maintaining the solution under stirring for 1 hour to 48 hours;
- c) precipitating the hyaluronic acid or salt thereof by adding a solvent selected from a (C1-C4) alkyl alcohol, such as methanol or isopropanol, or acetone;
- d) eliminating the impurities and any by-products with a series of washes in a mixture of water and a solvent selected from a (C1-C4) alkyl alcohol, such as methanol or isopropanol, or acetone.

"Pharmaceutical, injectable or ophthalmic grade" means hyaluronic acid or a salt thereof with a microbiological profile such as to meet the requirements set out in the pharmacopoeia for the corresponding degree of purity.

The pharmaceutical, injectable or ophthalmic grade hyaluronic acid or salt thereof prepared by the process according to the invention preferably has a maximum value of $10^3$ CFU/g and an endotoxin content of less than 0.5 EU/mg.

The hyaluronic acid salt is a salt acceptable for pharmaceutical or cosmetic use or in medical devices, such as the sodium, potassium, lithium or quaternary ammonium salt, for example tetrabutylammonium, preferably the sodium salt.

Step a) is preferably conducted at a temperature ranging between 80° C. and 100° C.

The solvent used in step a) is preferably formamide.

The solvent used for the precipitation in step c) is preferably acetone.

The precipitate obtained in step c) is preferably washed with a solvent selected from isopropanol and methanol, preferably methanol, and filtered.

The hyaluronic acid or salt thereof used in the process preferably has a weight average molecular weight ranging between $10^3$ and $10^6$ Daltons.

The process according to the invention produces hyaluronic acid or a salt thereof starting with the product with a lower degree of microbiological purity (e.g. cosmetic grade), giving rise to a product compatible with injectable (mesodermal, subdermal or intra-articular), pharmaceutical or ophthalmic application.

The starting hyaluronic acid is usually cosmetic grade.

To increase the degree of purification of the product, steps a), b), c), and d) of the process according to the invention can be repeated at least once.

The hyaluronic acid, or salt thereof, obtained by the process according to the invention has a microbiological profile compatible with use in pharmaceutical or dermocosmetic formulations or medical devices.

The hyaluronic acid obtained by the process according to the invention can be used in pharmaceutical or dermocosmetic formulations, comprising pharmaceutical, injectable or ophthalmic grade hyaluronic acid or an acceptable salt thereof, for use in the dermocosmetic or pharmaceutical field, in medical devices or as a supplement, either alone or with at least one excipient and/or carrier acceptable for pharmaceutical or dermocosmetic use or as a medical device.

EXAMPLES

Methods

Measurement of Endotoxin Level (LAL Test)

The endotoxins were quantitated with EU PHARMA method 0172018.20614, corresponding to USP 41 NF 36 2018 paras. 85-161.

The cosmetic grade hyaluronic acid sodium salt used for the following experimental tests possesses an endotoxin level evaluated by said method as 0.82 EU/mg.

Example 1: Preparation of Pharmaceutical Grade Hyaluronic Acid Sodium Salt MW 1500 kDa: (Step a) 95° C.: 1 h; Step b) 25° C.: 19 h)

200 ml of formamide was introduced into a 500 ml three-necked flask, followed by 10 g of cosmetic grade hyaluronic acid sodium salt with a molecular weight of 1500 kDa. The mixture was thermostated at 95° C. and maintained under stirring at a constant temperature for 1 h. The temperature was then reduced to 25° C. and the mixture was maintained under stirring for 19 h at the same temperature.

2.6 g of sodium chloride dissolved in 14 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.36 EU/mg.

Example 2: Preparation of Pharmaceutical Grade Hyaluronic Acid Sodium Salt MW 300 kDa: (Step a) 95° C.: 1 h; Step b) 25° C.: 19 h)

200 ml of formamide was introduced into a 500 ml three-necked flask, followed by 10 g of cosmetic grade hyaluronic acid sodium salt with a molecular weight of 300 kDa. The mixture was thermostated at 95° C. and maintained under stirring at a constant temperature for 1 h. The temperature was then reduced to 25° C. and the mixture was maintained under stirring for 19 h at the same temperature.

2.6 g of sodium chloride dissolved in 14 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.27 EU/mg.

Example 3: Preparation of Pharmaceutical Grade Hyaluronic Acid Sodium Salt MW 25 kDa: (Step a) 95° C.: 1 h; Step b) 25° C.: 19 h)

200 ml of formamide was introduced into a 500 ml three-necked flask, followed by 20 g of cosmetic grade hyaluronic acid sodium salt with a molecular weight of 25 kDa. The mixture was thermostated at 95° C. and maintained under stirring at a constant temperature for 1 h. The temperature was then reduced to 25° C. and the mixture was maintained under stirring for 19 h at the same temperature.

4 g of sodium chloride dissolved in 20 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.38 EU/mg.

Example 4: Preparation of Pharmaceutical Grade Hyaluronic Acid Sodium Salt MW 1500 kDa: (Step a) 95° C.: 1 h; Step b) 25° C.: 43 h)

200 ml of formamide was introduced into a 500 ml three-necked flask, followed by 5 g of cosmetic grade hyaluronic acid sodium salt with a molecular weight of 1500 kDa. The mixture was thermostated at 95° C. and maintained under stirring at a constant temperature for 1 h. The temperature was then reduced to 25° C. and the mixture was maintained under stirring for 43 h at the same temperature. 2.6 g of sodium chloride dissolved in 28 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.15 EU/mg.

Example 5: Preparation of Pharmaceutical Grade Hyaluronic Acid Sodium Salt MW 300 kDa: (Step a) 95° C.: 1 h; Step b) 25° C.: 43 h)

200 ml of formamide was introduced into a 500 ml three-necked flask, followed by 10 g of cosmetic grade hyaluronic acid sodium salt with a molecular weight of 300 kDa. The mixture was thermostated at 95° C. and maintained under stirring at a constant temperature for 1 h. The temperature was then reduced to 25° C. and the mixture was maintained under stirring for 43 h at the same temperature.

2.6 g of sodium chloride dissolved in 28 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.14 EU/mg.

Example 6: Preparation of Pharmaceutical Grade Hyaluronic Acid Sodium Salt MW 25 kDa: (Step a) 95° C.: 1 h; Step b) 25° C.: 43 h)

200 ml of formamide was introduced into a 500 ml three-necked flask, followed by 20 g of cosmetic grade hyaluronic acid sodium salt with a molecular weight of 25 kDa. The mixture was thermostated at 95° C. and maintained under stirring at a constant temperature for 1 h. The temperature was then reduced to 25° C. and the mixture was maintained under stirring for 43 h at the same temperature.

4 g of sodium chloride dissolved in 35 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.15 EU/mg.

Example 7: Preparation of Pharmaceutical Grade Hyaluronic Acid Sodium Salt MW 300 kDa: (Step a) 95° C.: 43 h; Step b) 25° C.: 1 h)

200 ml of formamide was introduced into a 500 ml three-necked flask, followed by 10 g of cosmetic grade hyaluronic acid sodium salt with a molecular weight of 300 kDa. The mixture was thermostated at 95° C. and maintained under stirring at a constant temperature for 43 h. The temperature was then reduced to 25° C., 2.6 g of sodium chloride dissolved in 28 ml of water for injection was added, and the mixture was left under stirring for 1 h at the same temperature.

The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of <0.05 EU/mg.

Example 8: Preparation of Pharmaceutical Grade Hyaluronic Acid Sodium Salt MW 25 kDa: (Step a) 95° C.: 1 h; Step b) 25° C.: 43 h)

300 ml of formamide was introduced into a 500 ml three-necked flask, followed by 6 g of cosmetic grade hyaluronic acid sodium salt with a molecular weight of 25 kDa. The mixture was thermostated at 95° C. and maintained under stirring at a constant temperature for 1 h. The temperature was then reduced to 25° C. and the mixture was maintained under stirring for 43 h at the same temperature.

3 g of sodium chloride dissolved in 15 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.12 EU/mg.

Example 9: Preparation of Pharmaceutical Grade Hyaluronic Acid Sodium Salt MW 300 kDa: (Step a) 95° C.: 17 h; Step b) 25° C.: 1 h)

200 ml of formamide was introduced into a 500 ml three-necked flask, followed by 20 g of cosmetic grade hyaluronic acid sodium salt with a molecular weight of 300 kDa. The mixture was thermostated at 95° C. and maintained under stirring at a constant temperature for 17 h. The temperature was then reduced to 25° C.

2.6 g of sodium chloride dissolved in 28 ml of water for injection was then added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.20 EU/mg.

Example 10: Preparation of Pharmaceutical Grade Hyaluronic Acid Sodium Salt MW 300 kDa: Repetition of Purification Process (Step a) 95° C.: 17 h; Step b) 25° C.: 1 h)

100 ml of formamide was introduced into a 500 ml three-necked flask, followed by 10 g of hyaluronic acid as obtained in Example 9. The mixture was thermostated at 95° C. and maintained under stirring at a constant temperature for 17 h. The temperature was then reduced to 25° C., 1.3 g of sodium chloride dissolved in 14 ml of water for injection was added, and the mixture was left under stirring for about 1 h. The product was isolated by precipitation in acetone and subsequent filtration.

The product underwent several washes with methanol, each followed by low-pressure filtration. The precipitate was dried at low pressure at room temperature for about 16 h in a laminar-flow hood.

A 5 g sample of product subjected to the LAL test proved to have an endotoxin content of 0.09 EU/mg.

The invention claimed is:

1. A process for the preparation of hyaluronic acid or a salt thereof, of pharmaceutical, injectable or ophthalmic grade, comprising the following steps:
   a) dissolving hyaluronic acid or a salt thereof at a temperature ranging between 50° C. and 100° C. in a solvent selected from dimethylformamide, dimethylacetamide, N-methylpyrrolidone and formamide, and keeping the solution under stirring at said temperature for a period of 1 hour to 48 hours;
   b) decreasing the temperature to room temperature and keeping the solution under stirring for 1 hour to 48 hours;
   c) precipitating hyaluronic acid or a salt thereof by adding a solvent selected from a (C1-C4) alkyl alcohol or acetone;
   d) removing impurities and any by-products by a series of washes in a mixture of water and a solvent selected from a (C1-C4) alkyl alcohol or acetone.

2. The process according to claim 1, wherein hyaluronic acid or a salt thereof, of pharmaceutical, injectable or ophthalmic grade, is hyaluronic acid or a salt thereof with a maximum value of $10^3$ CFU/g and an endotoxin content of less than 0.5 EU/mg.

3. The process according to claim 1, wherein the temperature of step a) ranges between 80° C. and 100° C.

4. The process according to claim 1, wherein the solvent used in step a) is formamide.

5. The process according to claim 1, wherein the solvent used in step c) for the precipitation is acetone.

6. The process according to claim 1, wherein the precipitated product obtained in step c) is washed with a solvent selected from isopropanol and methanol and filtered.

7. The process according to claim 6, wherein the precipitated product obtained in step c) is washed with methanol and filtered.

8. The process according to claim 1, wherein steps a), b), c) and d) are repeated at least once.

9. The process according to claim 1, wherein the solvent used in step c) for the precipitation is methanol or isopropanol.

* * * * *